US008562679B2

(12) United States Patent
Rechenberg

(10) Patent No.: US 8,562,679 B2
(45) Date of Patent: Oct. 22, 2013

(54) THREE LAYER BREAST PROSTHESIS

(75) Inventor: Joachim Rechenberg, Nussdorf A. In (DE)

(73) Assignee: American Breat Care, LP, Marietta, GA (US)

( * ) Notice: Subject to any disclaimer, the term of this patent is extended or adjusted under 35 U.S.C. 154(b) by 329 days.

(21) Appl. No.: 13/189,747

(22) Filed: Jul. 25, 2011

(65) Prior Publication Data

US 2012/0071973 A1 Mar. 22, 2012

Related U.S. Application Data

(60) Provisional application No. 61/383,558, filed on Sep. 16, 2010.

(51) Int. Cl.
*A61F 2/12* (2006.01)
(52) U.S. Cl.
USPC .................................................. 623/8
(58) Field of Classification Search
USPC .............................................. 623/7–8
See application file for complete search history.

(56) References Cited

U.S. PATENT DOCUMENTS

| | | | | | |
|---|---|---|---|---|---|
| 3,859,447 | A | * | 1/1975 | Sreenivasan | 426/73 |
| 3,963,627 | A | * | 6/1976 | Cottrell | 252/4 |
| 4,038,762 | A | * | 8/1977 | Swan, Jr. | 36/89 |
| 4,100,627 | A | | 7/1978 | Brill, III | |
| 4,108,928 | A | * | 8/1978 | Swan, Jr. | 264/417 |
| 4,172,298 | A | | 10/1979 | Rechenberg | |
| 4,243,754 | A | * | 1/1981 | Swan, Jr. | 521/55 |
| 4,247,351 | A | | 1/1981 | Rechenberg | |
| 4,249,975 | A | | 2/1981 | Rechenberg | |
| 4,426,742 | A | | 1/1984 | Prahl | |
| 4,795,464 | A | | 1/1989 | Eberl et al. | |
| 4,950,291 | A | | 8/1990 | Mulligan | |
| 5,035,249 | A | * | 7/1991 | Sasaki et al. | 128/899 |
| 5,071,433 | A | | 12/1991 | Naestoft et al. | |
| 5,352,307 | A | | 10/1994 | Wild | |
| 5,358,521 | A | * | 10/1994 | Shane | 623/8 |
| 5,411,541 | A | | 5/1995 | Bell et al. | |

(Continued)

FOREIGN PATENT DOCUMENTS

| | | |
|---|---|---|
| EP | 0 005 275 A1 | 5/1979 |
| EP | 0005275 A1 | 5/1979 |
| WO | 2011086537 A2 | 7/2011 |

OTHER PUBLICATIONS

PCT: "Notification of Transmittal of the International Search Report and the Written Opinion of the International Searching Authority, or the Declaration"; Jan. 29, 2013; KIPO.

*Primary Examiner* — Suzette J Gherbi
(74) *Attorney, Agent, or Firm* — Bockhop & Associates, LLC; Bryan W. Bockhop

(57) ABSTRACT

A breast prosthesis that includes an outer first layer, a middle second layer and an inner third layer. The outer first layer includes a first material that has a first firmness. The first firmness allows for a 20 mm to a 25 mm penetration by a cone penetrometer. The first layer has a shape corresponding to a shape of a breast form. The middle second layer is disposed adjacent to the first layer and includes a second material that has a second firmness that is greater than the first firmness. The inner third layer is disposed adjacent to the second layer opposite from the first layer and includes a third material that has a third firmness that is less than the second firmness.

20 Claims, 2 Drawing Sheets

(56) References Cited

U.S. PATENT DOCUMENTS

| | | |
|---|---|---|
| 5,549,671 A | 8/1996 | Waybright et al. |
| 5,584,883 A | 12/1996 | Wild |
| 5,738,812 A | 4/1998 | Wild |
| 5,792,292 A | 8/1998 | Wild |
| 5,895,423 A | 4/1999 | Becker et al. |
| 5,922,023 A | 7/1999 | Mulligan |
| 5,925,282 A | 7/1999 | Rasmussen |
| 6,086,450 A | 7/2000 | Mankovitz |
| 6,162,250 A * | 12/2000 | Malice, Jr. et al. ............ 623/7 |
| 6,296,800 B1 | 10/2001 | Stelter et al. |
| 6,342,117 B1 | 1/2002 | Reitmaier et al. |
| 6,361,397 B1 | 3/2002 | Mankovitz et al. |
| 6,443,986 B1 * | 9/2002 | Malice et al. ............ 623/7 |
| 6,451,139 B1 * | 9/2002 | Weber-Unger et al. ......... 156/61 |
| 6,494,912 B2 | 12/2002 | Reitmaier et al. |
| 7,306,568 B2 | 12/2007 | Diana |
| 7,347,871 B2 | 3/2008 | Schneider-Nieskens |
| 2002/0038147 A1 | 3/2002 | Miller, III |
| 2002/0193878 A1 | 12/2002 | Bowman et al. |
| 2005/0197698 A1 | 9/2005 | Schneider-Nieskens |
| 2006/0036266 A1 | 2/2006 | Sulamanidze et al. |
| 2007/0135916 A1 | 6/2007 | Maxwell et al. |
| 2007/0267131 A1 | 11/2007 | Reitmeter et al. |
| 2007/0293945 A1 | 12/2007 | Snyder |
| 2009/0216323 A1 | 8/2009 | Ledergerber |
| 2009/0255618 A1 | 10/2009 | Tassone et al. |
| 2013/0131798 A1 * | 5/2013 | Wollnick et al. ............ 623/8 |

* cited by examiner

THREE LAYER BREAST PROSTHESIS

CROSS-REFERENCE TO RELATED APPLICATION(S)

This application claims the benefit of U.S. Provisional Patent Application Ser. No. 61/383,558, filed Sep. 16, 2010, the entirety of which is hereby incorporated herein by reference.

BACKGROUND OF THE INVENTION

1. Field of the Invention

The present invention relates to breast prostheses and, more specifically, to a multi-chamber breast prosthesis.

2. Description of the Related Art

Many women who have had a mastectomy wear a breast prosthesis at the affected site. Typically, a breast prosthesis is made to look like a natural breast. It is placed against the patient's chest and is typically supported by a brassiere.

A common type of breast prosthesis is made from a soft silicone gel. Such a prosthesis includes an envelope made from a thin plastic film into which uncured silicone gel is injected. The pouch and the uncured silicone gel are then placed in a metallic mold having an interior that is complementary in shape to the desired shape of the prosthesis. The mould is then placed in an oven, where the silicone gel is heated until it is cured.

The silicone gel must be cured until it has a firmness so that it will maintain the shape of a natural breast during regular use. However, prostheses having such firmness have two disadvantages: (1) they can be uncomfortable when placed against the chest of the user; and (2) their outer surface does not drape naturally, thereby giving user an unnatural, asymmetric appearance.

Therefore, there is a need for a breast prosthesis that is firm enough to maintain a natural breast form shape during regular use, but that is comfortable to wear and that gives a natural drape.

SUMMARY OF THE INVENTION

The disadvantages of the prior art are overcome by the present invention which, in one aspect, is a breast prosthesis that includes an outer first layer, a middle second layer and an inner third layer. The outer first layer includes a first material that has a first firmness. The first firmness allows for a 20 mm to a 25 mm penetration by a cone penetrometer. The first layer has a shape corresponding to a shape of a breast form. The middle second layer is disposed adjacent to the first layer and includes a second material that has a second firmness that is greater than the first firmness. The inner third layer is disposed adjacent to the second layer opposite from the first layer and includes a third material that has a third firmness that is less than the second firmness.

In another aspect, the invention is a breast form prosthesis that includes four films that are welded together at a single weld to form three chambers having a shape of a breast form footprint. The three chambers include: a first chamber, a second chamber and a third chamber. An outer first layer is disposed in the first chamber and includes a first material that has a first firmness. The first layer has a shape corresponding to a shape of a breast form. The first material includes a silicone gel with a first concentration of a methyl hydrosiloxane polymer cross-linker. The middle second layer is disposed adjacent to the first layer in the second chamber and includes a second material that has a second firmness that is greater than the first firmness. The second material includes a silicone gel with a second concentration, greater than the first concentration, of a methyl hydrosiloxane polymer cross-linker. The inner third layer is disposed in the third chamber and adjacent to the second layer opposite from the first layer. The inner third layer includes a third material that has a third firmness that is less than the second firmness. The third material includes a silicone gel with a third concentration, less than the second concentration, of a methyl hydrosiloxane polymer cross-linker.

In yet another aspect, the invention is a method of making a breast prosthesis, in which four flexible films are welded together with a single weld so as to form a breast form envelope. The breast form envelope includes a first chamber, a second chamber and a third chamber. Each chamber has a shape of a breast form footprint. The breast form envelope is placed into a mold having a shape that is complementary in shape to a breast form. A first material is injected into the first chamber. The first material has a first firmness that allows for a 20 mm to a 25 mm penetration by a cone penetrometer when cured. A second material is injected into the second chamber. The second material has a second firmness when cured. The second firmness is greater than the first firmness. A third material is injected into the third chamber. The third material has a third firmness when cured. The third firmness is less than the second firmness. The mold, the breast form envelope, the first material, the second material and the third material are heated to a temperature sufficient to cure the first material to the first firmness, the second material to the second firmness and the third material to the third firmness.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
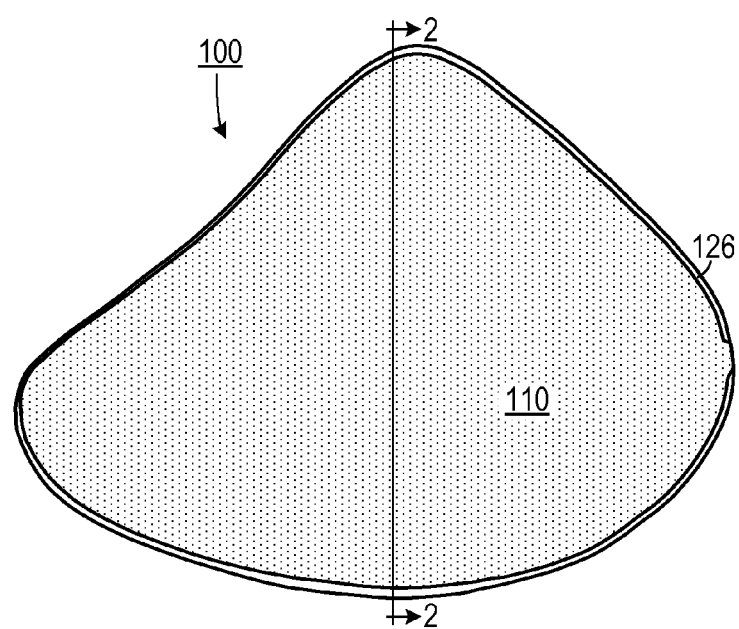
FIG. 1 is a front elevational view of one embodiment of a three layer breast prosthesis.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

U.S. Pat. Nos. 4,247,351 and 4,249,975 disclose prostheses of silicone gel encased in polyurethane film and, therefore, are incorporated herein by reference. U.S. Pat. Nos. 4,950,291, 5,895,423, 5,922,023 and 7,759,354 disclose multi-chambered breast prosthesis and methods of making the same and are also, therefore, incorporated herein by reference.

One embodiment of a breast prosthesis includes three layers of silicone gel enclosed in polyurethane film. The shape of the prosthesis conforms to the shape of a female breast. The layers of silicone are arranged such that a layer of soft conformable silicone is closest to the chest of the wearer and can conform to any irregularities in the chest. The middle layer of silicone is firm and provides support for the prosthesis, and the third layer of silicone positioned in the front of prosthesis (furthest away from the body) is soft and provides a natural drape to the prosthesis, which gives the wearer's chest a natural look and a symmetric appearance.

Figure 2:
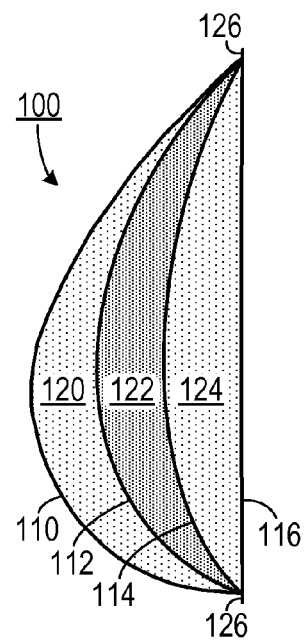
FIG. 2 is a cross-sectional view of the breast prosthesis shown in FIG. 1 taken along line 2-2.
Figure 3A:
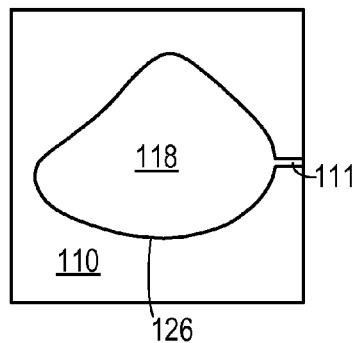
FIGS. 3A-3F are a series of schematic drawings showing one method of making a breast prosthesis.
Figure 3B:
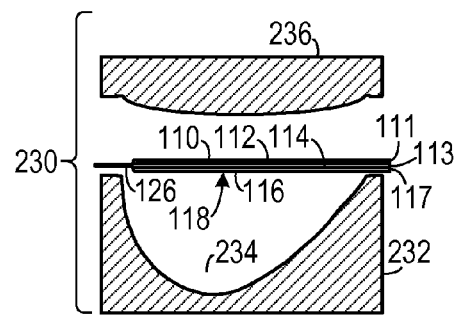
Figure 3C:
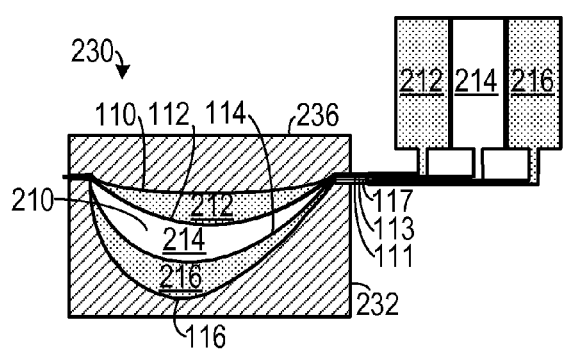
Figure 3D:
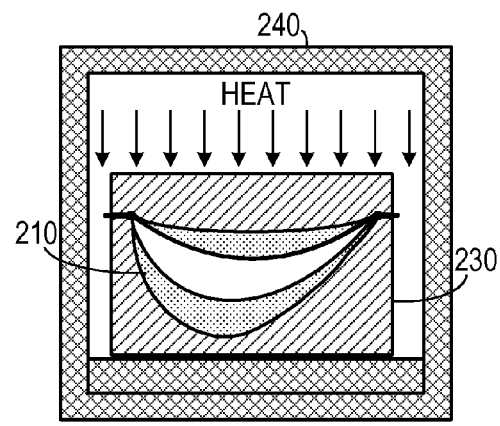
Figure 3E:
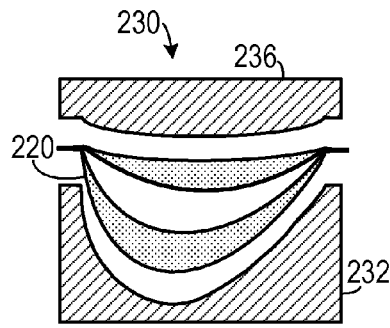
Figure 3F:
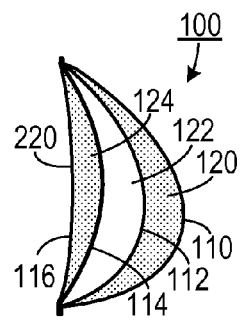

As shown in FIGS. 1 and 2, one embodiment of a three layer breast prosthesis 100 includes an exterior layer 120 that is relatively soft, a middle layer 122 that is relatively firm and an interior layer 124 that is also relatively soft. Each of the layers, 120, 122 and 124, typically include a silicone gel with the middle layer 122 including a higher concentration of cross-linker to give it additional firmness. The layers are held in flexible chambers that would typically include polyurethane film (typically of about 60 micron to 90 micron thickness) that are sealed together along their periphery along a single weld 126.

In one embodiment, a first polyurethane film 110, a second polyurethane film 112, a third polyurethane film 114 and a fourth polyurethane film 116 are welded together along a single weld 126 to form three chambers. The single weld 126 has the footprint of a breast form. The first material of the first layer 120 is placed in a first of the three chambers. The second material of the second layer 122 is placed in a second of the three chambers. The third material of the third layer 124 is placed in a third of the three chambers.

The first material, the second material and the third material can each include silicone gels. In one embodiment, the silicone gels include a two-component addition-cure silicone gel composition that includes a first combination, including a vinyl polymer, a silicone oil and a cross-linker, and a second combination, including a vinyl polymer, a silicone oil and a catalyst (such as a platinum and silicone complex). (One example of suitable silicon gels include prosthesis gels manufactured by Wacker Chemie GmbH.) A typical cross-linker includes a methyl hydrosiloxane polymer.

In one embodiment the exterior layer 120 and the interior layer 124 have a firmness that allows for a 20 mm to a 26 mm penetration by a cone penetrometer when cured and the middle layer 122 has a firmness that allows for a 10 mm to a 13 mm penetration by a cone penetrometer when cured. In one embodiment, micro-spheres can be added to one or all of the silicone gels to reduce the weight of the resulting prosthesis 100. Similarly, pigments can be added to give the prosthesis a natural look.

In one experimental embodiment, all silicone gel penetrations were determined on a Humboldt H1200 penetrometer. The probe employed a 65 mm diameter cone (the dimensions corresponded to part number 18-0122 from Petrolab Company) and the total probe weight was 24.9 g.

This breast prosthesis 100 provides a soft back layer 124 that conforms to the chest of the wearer and also a soft front layer 120 that provides a natural drape and fit. The middle layer 122 has sufficient firmness to maintain the shape of the breast form during regular use.

In one embodiment of a method of making a breast form, as shown in FIGS. 3A-3F, four sheets of polyurethane film (110, 112, 114 and 116) are welded together along a single weld 126 thereby forming an envelope 118 that includes three different chambers and that has a shape corresponding to a desired breast form. The breast form can be a-symmetric (as in the example shown in FIG. 1) or it can be symmetric. The weld includes a corresponding three sprue inlets (111, 113 and 117) that open the chambers to the outside. The envelope 118 is placed in a mold 230 including a front portion 232 and a back portion 236. The mold 230 defines a cavity 234 having a shape that is complementary to the desired shape of a breast form.

Once in the mold 230, the first material 212 is injected into the first chamber through the first sprue 111, the second material 214 is injected into the second chamber through the second sprue 113 and the third material 216 is injected into the third chamber through the third sprue 117. This forms an uncured breast form 210, from which any air is removed. The sprues (111, 113 and 117) are sealed and the mold 230 with the uncured breast form 210 therein is placed in an oven 240 and heated to a sufficient temperature for a sufficient amount of time to cure the first material 212, the second material 214 and the third material 216, thereby forming a cured breast form 220. The exact temperature and time depend on the specific mixture of silicone gel used; however, it can readily be determined from the manufacturer's data sheet. The cured breast form 220 is removed from the oven 240, is allowed to cool, removed from the mold 230 and any excess film is trimmed away from the weld, resulting in a breast prosthesis 100.

The final prosthesis 100 includes a layer 124 closest to the patient that is soft and conforms to the chest of the wearer for comfort. The middle layer 122 is firm and provides a stable structure to the prosthesis. The front layer 120 is soft enough to provide a natural drape to the prosthesis 100 so as to give it an appearance of natural breast tissue.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A breast prosthesis, comprising:
   (a) an outer first layer including a first material that has a first firmness that allows for a 20 mm to a 25 mm penetration by a cone penetrometer, the first layer having a shape corresponding to a shape of a breast form;
   (b) a middle second layer disposed adjacent to the first layer and including a second material that has a second firmness that is greater than the first firmness; and
   (c) an inner third layer disposed adjacent to the second layer opposite from the first layer and including a third material that has a third firmness that is less than the second firmness,
   wherein at least one of the first material, the second material and the third material comprises micro-spheres added thereto so as to reduce the weight of the breast prosthesis.

2. A breast prosthesis, comprising:
   (a) an outer first layer including a first material that has a first firmness that allows for a 20 mm to a 25 mm penetration by a cone penetrometer, the first layer having a shape corresponding to a shape of a breast form;
   (b) a middle second layer disposed adjacent to the first layer and including a second material that has a second firmness that is greater than the first firmness;

(c) an inner third layer disposed adjacent to the second layer opposite from the first layer and including a third material that has a third firmness that is less than the second firmness; and (d) four films that are welded together to form three chambers having a shape of a breast form footprint, the three chambers including: a first chamber into which the first material is disposed, a second chamber into which the second material is disposed and a third chamber into which the third material is disposed.

3. The breast prosthesis of claim 2, wherein the four films each comprise a polyurethane film.

4. The breast prosthesis of claim 2, wherein the four films are welded together at a single weld.

5. The breast prosthesis of claim 1, wherein the firmness of the second material is such that the second material allows for a 10 mm to a 13 mm penetration by a cone penetrometer.

6. The breast prosthesis of claim 1, wherein the firmness of the third material is such that the third material allows for a 22 mm to a 26 mm penetration by a cone penetrometer.

7. The breast prosthesis of claim 1, wherein the first material comprises silicone gel with a first concentration of a cross-linker, the second material comprises silicone gel with a second concentration of cross-linker, and the third material comprises silicone gel with a third concentration of cross-linker, wherein the second concentration is greater that both the first concentration and the third concentration.

8. The breast prosthesis of claim 7, wherein the cross-linker comprises a methyl hydrosiloxane polymer.

9. The breast prosthesis of claim 1, further comprising four films that are welded together to form three chambers having a shape of a breast form footprint, the three chambers including: a first chamber into which the first material is disposed, a second chamber into which the second material is disposed and a third chamber into which the third material is disposed.

10. The breast prosthesis of claim 9, wherein the four films each comprise a polyurethane film.

11. The breast prosthesis of claim 9, wherein the four films are welded together at a single weld.

12. The breast prosthesis of claim 2, wherein the firmness of the second material is such that the second material allows for a 10 mm to a 13 mm penetration by a cone penetrometer.

13. The breast prosthesis of claim 2, wherein the firmness of the third material is such that the third material allows for a 22 mm to a 26 mm penetration by a cone penetrometer.

14. The breast prosthesis of claim 2, wherein the first material comprises silicone gel with a first concentration of a cross-linker, the second material comprises silicone gel with a second concentration of cross-linker, and the third material comprises silicone gel with a third concentration of cross-linker, wherein the second concentration is greater that both the first concentration and the third concentration.

15. The breast prosthesis of claim 14, wherein the cross-linker comprises a methyl hydrosiloxane polymer.

16. The breast prosthesis of claim 2, wherein at least one of the first material, the second material and the third material comprises micro-spheres added thereto so as to reduce the weight of the breast prosthesis.

17. A breast prosthesis, comprising:

(d) an outer first layer including a first material that has a first firmness that allows for a 20 mm to a 25 mm penetration by a cone penetrometer, the first layer having a shape corresponding to a shape of a breast form;

(e) a middle second layer disposed adjacent to the first layer and including a second material that has a second firmness that is greater than the first firmness; and (f) an inner third layer disposed adjacent to the second layer opposite from the first layer and including a third material that has a third firmness that is less than the second firmness;

(g) four films that are welded together to form three chambers having a shape of a breast form footprint, the three chambers including: a first chamber into which the first material is disposed, a second chamber into which the second material is disposed and a third chamber into which the third material is disposed, wherein at least one of the first material, the second material and the third material comprises micro-spheres added thereto so as to reduce the weight of the breast prosthesis.

18. The breast prosthesis of claim 17, wherein the firmness of the second material is such that the second material allows for a 10 mm to a 13 mm penetration by a cone penetrometer.

19. The breast prosthesis of claim 17, wherein the firmness of the third material is such that the third material allows for a 22 mm to a 26 mm penetration by a cone penetrometer.

20. The breast prosthesis of claim 17, wherein the first material comprises silicone gel with a first concentration of a methyl hydrosiloxane polymer cross-linker, the second material comprises silicone gel with a second concentration of methyl hydrosiloxane polymer cross-linker, and the third material comprises silicone gel with a third concentration of methyl hydrosiloxane polymer cross-linker, wherein the second concentration is greater that both the first concentration and the third concentration.

* * * * *